United States Patent
Paolini et al.

(10) Patent No.: US 6,206,873 B1
(45) Date of Patent: Mar. 27, 2001

(54) DEVICE AND METHOD FOR ELIMINATING ADIPOSE LAYERS BY MEANS OF LASER ENERGY

(75) Inventors: Cesare Paolini, Montanino di Reggello; Maurizio Maida, Marina di Massa; Fabrizio Mencarelli, Fivizzano, all of (IT)

(73) Assignee: EL. EN. S.P.A. (IT)

(*) Notice: Subject to any disclaimer, the term of this patent is extended or adjusted under 35 U.S.C. 154(b) by 0 days.

(21) Appl. No.: 09/322,579

(22) Filed: May 28, 1999

Related U.S. Application Data

(63) Continuation-in-part of application No. 08/798,516, filed on Feb. 10, 1997.

(30) Foreign Application Priority Data

Feb. 13, 1996 (IT) .............................................. FI96A0025

(51) Int. Cl.[7] .................................................. A61F 7/60
(52) U.S. Cl. .................. 606/7; 606/15; 606/16
(58) Field of Search ............................. 606/7, 10, 13–17

(56) References Cited

U.S. PATENT DOCUMENTS

| 5,102,410 | * | 4/1992 | Dressel ..................................... 606/7 |
| 5,334,190 | * | 8/1994 | Seller ..................................... 606/16 |
| 5,470,330 | * | 11/1995 | Goldenberg et al. ..................... 606/7 |
| 5,649,924 | * | 7/1997 | Everett et al. .......................... 606/15 |
| 5,807,385 | * | 9/1998 | Keller ..................................... 606/9 |
| 6,106,516 | * | 8/2000 | Massengill ............................. 606/15 |

* cited by examiner

Primary Examiner—Robert L. Nasser
(74) Attorney, Agent, or Firm—McGlew and Tuttle, P.C.

(57) ABSTRACT

A device and method for the removal of subcutaneous adipose layers with a laser source, optical fiber for conveying the laser ben emitted by the first source and a hollow needle f or guiding the fiber. The fiber ends in the vicinity of the end of the needle. The laser beam is generated with an intensity and a wavelength for liquefying, and maintaining liquid, the adipose cells. The laser beam from the optical fiber irradiates adipose cells in the adipose layer to transform the adipose cells into, and maintain the adipose cells as, a liquid substance.

19 Claims, 1 Drawing Sheet

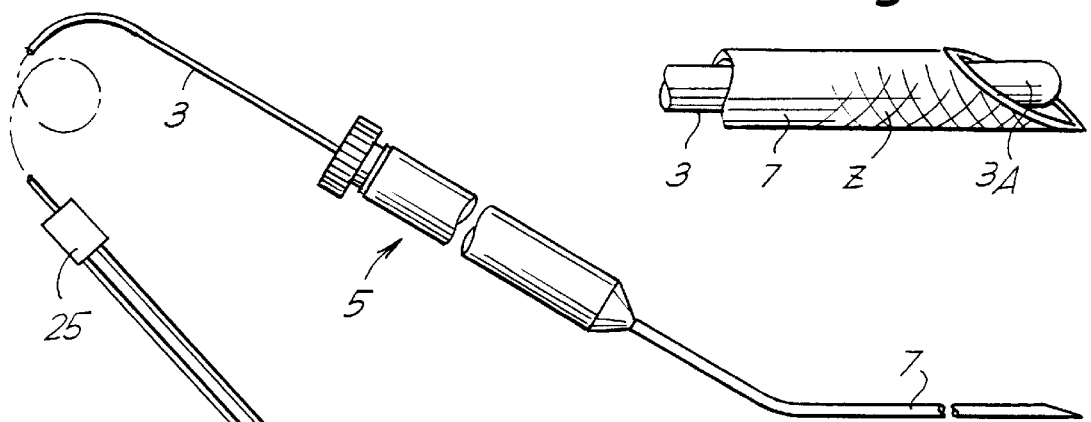
Fig. 3
Fig. 1
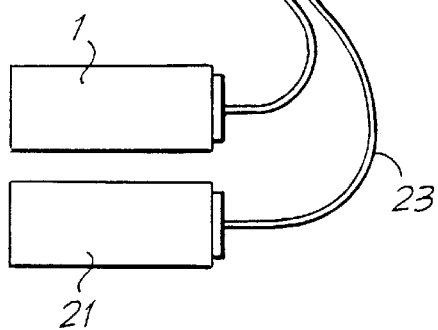
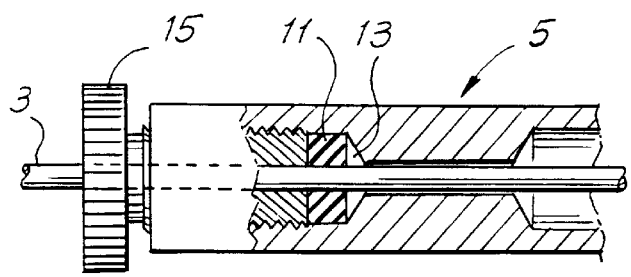
Fig. 2
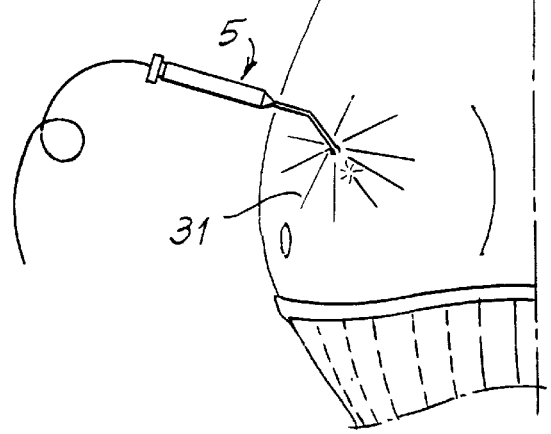
Fig. 4

DEVICE AND METHOD FOR ELIMINATING ADIPOSE LAYERS BY MEANS OF LASER ENERGY

This application is a continuation-in-part of Ser. No. 08/798,516 filed Feb. 10, 1997.

FIELD OF THE INVENTION

The present invention relates to a device for eliminating adipose layers and to an associated technique for carrying out this elimination using the device.

BACKGROUND OF THE INVENTION

The reduction of subcutaneous adipose layers constitutes one of the most important areas of aesthetic treatments Two techniques currently exist for this purpose. The first technique, known as liposuction, consists of introduction into the adipose layers of probes roughly 5 mm in diameter through holes made in the skin of the patient undergoing treatment, for suction and removal of fat. This technique has a number of disadvantages, such as the creation of a lack of homogeneity in the form of depressions in the zone of insertion of the probe which are visible from the outside, as well as excessive bleeding of the patient undergoing treatment. Furthermore, both the cells of fat and the stroma are sucked out non-selectively.

The second technique utilizes subcutaneous ultrasonic probes to rupture the membrane of the adipose cells, thus causing the escape of liquid which then has to be sucked out subsequently. In this case, suction of the stroma is not brought about and bleeding is therefore more limited. However, the disadvantage of the lack of homogeneity of the treatment remains.

SUMMARY AND OBJECTS OF THE INVENTION

The primary aim of the present invention is to produce a device and an associated method for eliminating adipose layers which do not have the disadvantages mentioned above.

In particular, a first aim of the present invention is the production of a device and a method which allow uniform treatment.

A further aim is the production of a device and a method which allow selective elimination of the adipose cells without damaging the stroma.

Yet another aim of the present invention is the production of a device and a method which eliminate the problem of bleeding and which reduce the dimensions of the holes for insertion of the probes.

These and other aims and advantages, which will be clear to experts in the field from reading the text which follows, are obtained essentially with a device which comprises a first laser source, optical fiber conveying means for conveying the laser beam emitted by said first source, and a hollow needle for guiding the fiber. The fiber ends in the vicinity of the end of the needle. A laser source generates a laser beam through the optical fiber with an intensity and a wavelength for liquefying, and maintaining liquid, the adipose cells. The intensity and wavelength of the laser beam ruptures membranes of the adipose cells and maintains collagen in the adipose layer substantially unaltered or undamaged. Blood vessels in the adipose layer are either also substantially undamaged, especially the large blood vessels, or any blood vessels that are damaged are cauterized, especially the small blood vessels.

With this device, it is possible to implement a method for the reduction of subcutaneous adipose layers, on the basis of introducing into the subcutaneous adipose layers a laser beam at an intensity and at a wavelength which are such that the lipolysis of the adipose cells is brought about, that is a rupturing of the membranes of the cells themselves, with consequent transformation of the adeps into a liquid substance which is then sucked out or preferably left in place in order to be drained by the lymphatic system and by the action of the phagocytes of the patient. In addition to a clear reduction in traumatism and greater selectivity of the method implemented in this manner in comparison with the liposuction system, the advantage is also obtained that the energy of the laser beam can be used to cauterize the small blood vessels which may be damaged by the insertion of the needle into the adipose layers. Loss of blood is thus virtually completely eliminated.

The most important aspect to be highlighted in the area treated by the present invention, is the fact that the collagen fibers remain intact even where the adipose layer has been removed. The presence of the collagen structure is very important for the reconstruction of healthy (non-fatty) tissue in the area where the adeps has been removed.

Usual liposuction techniques remove by suction entire pieces of adipose tissue and together therewith they also remove portions of blood vessels and collagen fibers. Thus present liposuction intervention is heavily invasive. The area under the skin where the collagen fibers have been removed together with the adipose tissue shows depressions and "sinkings" which are highly unaesthetical. Reconstruction of healthy (non-adipose) tissue in these areas is slow and unsatisfactory, due to the reduced vascularization and to the absence (or reduced presence) of collagen.

The method of the present invention is novel and advantageous over the art because it overcomes the above mentioned drawbacks. The method is mainly characterized in that the adipose tissue is removed by lysis, i.e. by rupturing the membranes of the cells forming the adipose layer. As a consequence, the adipose tissue is transformed into a liquid. The liquid thus obtained may be partially or totally suctioned away by means of a vacuum pump, quite in the same way as in the usual techniques. The difference is, however, the material removed through the suction cannula is substantially liquid and a much reduced impact on the patient is obtained. It is obviously easier and less painful to suck a liquid (generated by lipolysis) than pieces of adipose tissue which are solid. The collagen fibers and blood vessels are not damaged by the lysis effect of the laser and remain intact. The subsequent suction does not suck the collagen fibers nor the blood vessels away, as it happens in the traditional liposuction techniques. Subsequent recovery of the healthy tissue is easier.

As an alternative the liquid substance is left inside the body of the patient. In this case the liquid obtained by lysis of the adipose cells is slowly re-absorbed through the organism of the patient himself, namely through action of the lymphatic system and the phagocytes. This second method is slower than the former one, but is even less invasive and less traumatic.

In practice, the needle is borne by a hand unit which, in order to be more easily maneuverable, is inclined in relation to the needle.

In addition to a laser source which emits at a wavelength and at a power which are such that lipolysis is brought about, it is possible, with the same optical fiber, or with an additional optical fiber guided in the same needle, to convey into the adipose layers a beam of visible light which makes possible transcutaneous vision during implementation of the method.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a diagram of the device;

FIG. 2 is an enlarged longitudinal section view of the hand unit of the device in FIG. 1;

FIG. 3 is an enlarged view of the point of the needle, and

FIG. 4 is a view of the device being used in an example of application.

DESCRIPTION OF THE PREFERRED EMBODIMENT

With reference initially to FIG. 1, the device comprises a laser source 1 of the NdYAG type, with which an optical fiber 3 is associated, which conveys the energy of the source 1 toward a hand unit 5 equipped with a hollow guide needle 7 with a beveled end (FIG. 3). The needle has an external diameter of, for example, roughly I mm. The terminal end 3A of the optical fiber 3 ends at the point of the needle. The laser source 1 generates a laser beam through the optical fiber 3 with an intensity and a wavelength for liquefying, and maintaining liquid, the adipose cells. The intensity and wavelength of the laser beam ruptures membranes of the adipose cells and maintains collagen in the adipose layer substantially unaltered or undamaged. Blood vessels in the adipose layer are either also substantially undamaged, especially the large blood vessels, or any blood vessels that are damaged are cauterized, especially the small blood vessels.

In the example illustrated, the needle has an inclination in relation to the hand unit 5 of roughly 10–30 degrees and preferably 15–20 degrees to facilitate its use.

In FIG. 2, a possible system of fixing the fiber 3 can be seen, which comprises an elastic sleeve 11 accommodated in a seat 13, through which the fiber 3 passes and which is clamped by means of a threaded ring nut 15.

In the example illustrated, the device comprises a second laser source 21 which emits radiation in the visible range which is conveyed by means of a second optical fiber 23 to a connector 25, in which the visible radiation emitted by the laser 21 is introduced into the fiber 3. In this manner, the optical fiber 3 conveys to the point of the needle 7 a laser beam in the visible range also which allows the operator, in reduced ambient light, to follow accurately (by transcutaneous vision permitted by the transparency of the skin) the position of the end of the fiber and therefore to control the instantaneous point of application of the laser energy generated by the source 1.

The laser source 1 emits a beam which is preferably pulsed, at a wavelength between 0.75 and 2.5 micrometers, for example at 1.06 micrometers, with an energy level between 30 and 300 mjoules per pulse. The wavelength is preferably between 0.8 to 1.1 micrometers and the pulse frequency is between 10 and 60 Hz, preferably between 30 and 50 Hz and most preferably around 40 Hz.

The device described above is used by inserting the fiber subcutaneously into the patient, in the adipose layer to be eliminated. The end of the fiber 3 thus comes directly into contact with the adipose layer. The laser beam, in the appropriate dosage, brings about the rupturing of the membranes of the adipose cells and at the same time cauterizes the very small veins contained in the stroma, which can be easily damaged by the penetration of the needle 7. In this manner, the adeps becomes liquid and at the same time a local hemostasis is created. The liquefied fat is then absorbed by the body by lymphatic drainage and the action of the phagocytes, while subsequent intervention, similar to that carried out in the case of treatment with ultrasonic probes, to remove the liquefied fat is also possible.

In practice, the needle 7 is provided with a skin cutting tip and used to cut or pierce the skin of the patient. The needle is initially inserted subcutaneously and is then moved forward and backward by the operator to irradiate the adipose cells and cause lipolysis of the adipose layer and rupture membranes of the cells forming the adipose layer, thus transforming adeps forming the adipose layer into a liquid substance. The laser beam is generated and the irradiating performed to maintain the adipose cells as a liquid substance. The time which is necessary for the above depends on the characteristics of the tissue which is easily determined by the operator. Typically, to achieve the lipolysis of an adequate quantity of adipose cells, treatment with an energy level of 100 mjoules for a time of 200 microseconds per pulse is appropriate. The needle is kept in each penetration hole for a few minutes.

The liquid substance can then be removed by suctioning said liquid substance away from the adipose layer though a passage in the device or by another tool inserted through the skin of the patient. In another embodiment of the present invention the needle is removed from the patient leaving the liquid substance in the patient. The liquid substance is then left to be absorbed through elements of the patient adjacent the adipose cells, namely through the lymphatic system and phagocytes of the patient.

The movement of the point of the needle is easily controlled by means of the transcutaneous vision allowed by the visible laser beam generated by the second source 21. Lipolysis action is thus brought about in a certain portion of tissue. By extracting the needle and inserting it subcutaneously in an adjacent position, a subsequent portion of tissue is treated. From one and the same entry hole, the needle 7 can be inserted in various radial directions, treating an entire area of the tissue, as can be seen in FIG. 4, where 31 indicates in broken lines as a guide the insertion lines of the needle 7.

The end part of the needle 7 can be knurled in order to cause, during penetration of the adipose layers, a rupturing of the adipose cells and therefore in order to obtain greater effectiveness of treatment. In FIG. 3, the knurling is indicated diagrammatically by Z.

It is intended that the drawing shows only an example given only by way of practical demonstration of the invention, it being possible for the invention to vary in form and arrangement without moreover leaving the scope of the concept which forms the invention itself.

While specific embodiments of the invention have been shown and described in detail to illustrate the application of the principles of the invention, it will be understood that the invention may be embodied otherwise without departing from such principles.

What is claimed is:

1. A method for the removal of subcutaneous adipose layers, the method comprising the steps of:
   providing a hollow needle with a tip;
   providing a laser source with emitting characteristics for generating a laser beam having an intensity and a wavelength for causing lipolysis of adipose cells;
   generating a laser beam with said laser source;
   arranging an optical fiber inside said needle with one end of said optical fiber adjacent to said tip of said needle and with another end of said fiber connected to an output of said laser source;
   piercing the skin of a patient and bringing said needle tip into a subcutaneous adipose layer of the patient;
   irradiating said adipose layer with said laser beam to cause lipolysis of said adipose layer and rupturing membranes of cells forming the adipose layer, thus transforming adeps forming said adipose layer into a liquid substance.

2. The method in accordance with claim 1, further comprising:
   suctioning said liquid substance away from the adipose layer.

3. The method in accordance with claim 1, further comprising:
   removing said hollow needle from the patient leaving said liquid substance in place, said liquid substance being subsequently absorbed by the organism of the patient.

4. The method in accordance with claim 1, wherein:
   said tip of said needle includes a sharp edge;
   said piercing of the skin is performed with said needle.

5. The method in accordance with claim 4, further comprising:
   suctioning said liquid substance away from the adipose layer.

6. The method in accordance with claim 4, further comprising:
   removing said hollow needle from the patient leaving said liquid substance in place, said liquid substance being subsequently absorbed by the organism of the patient.

7. The method in accordance with claim 1, wherein:
   said generating of said laser beam and said irradiating is performed to cauterize blood vessels in the adipose layer damaged by said irradiating.

8. The method in accordance with claim 1, further comprising:
   irradiating the adipose layer with another laser beam to provide transcutaneous vision.

9. The method in accordance with claim 1, wherein:
   said generating is performed to generate said laser beam as a pulsed laser beam.

10. The method in accordance with claim 1, wherein:
    said generating is performed to generate said laser beam as a pulsed laser beam with a wavelength 0.75 and 2.5 micrometers, and with an energy level between 30 and 300 mjoules per pulse.

11. The method in accordance with claim 1, wherein:
    said generating is performed to generate said laser beam as a pulsed laser beam with a pulse frequency between 10 and 60 Hz, with a wavelength between 0.75 and 2.5 micrometers, and with an energy level between 30 and 300 mjoules per pulse.

12. The method in accordance with claim 1, wherein:
    said pulse frequency is between 40 and 50 Hz.

13. A method for treating adipose cells in a patient, the method comprising the steps of:
    providing a hollow needle with a tip and an optical fiber inside said needle with one end of said optical fiber adjacent to said tip of said needle;
    generating a laser beam through said optical fiber with an intensity and a wavelength for liquefying, and maintaining liquid, the adipose cells;
    moving said tip of said needle into a subcutaneous adipose layer of the patient;
    irradiating adipose cells in the adipose layer with said laser beam from said optical fiber to transform the adipose cells into, and maintain the adipose cells as, a liquid substance.

14. The method in accordance with claim 13, wherein:
    said generating of said laser beam and said irradiating is performed to rupture membranes of the adipose cells without substantially damaging collagen in the adipose layer.

15. The method in accordance with claim 13, wherein:
    said generating of said laser beam and said irradiating is performed to rupture membranes of the adipose cells and maintain both collagen and blood vessels in the adipose layer substantially unaltered.

16. The method in accordance with claim 13, further comprising:
    suctioning said liquid substance away from the adipose layer.

17. The method in accordance with claim 13, further comprising:
    removing said needle from the patient leaving said liquid substance in the patient;
    absorbing said liquid substance through elements of the patient adjacent the adipose cells.

18. The method in accordance with claim 17, wherein:
    said absorbing is through a lymphatic system and phagocytes of the patient.

19. The method in accordance with claim 13, further comprising:
    providing said needle with a skin cutting tip;
    cutting a skin of the patient with said skin cutting tip of said needle.

* * * * *

UNITED STATES PATENT AND TRADEMARK OFFICE
CERTIFICATE OF CORRECTION

PATENT NO. : 6,206,873 B1 Page 1 of 1
DATED : March 27, 2001
INVENTOR(S) : Paolini et al.

It is certified that error appears in the above-identified patent and that said Letters Patent is hereby corrected as shown below:

<u>Title page,</u>
Item [75], Inventors, should read: -- Cesare Paolini, Firenze
Maurizio Maida, Massa Carrara
Fabrizio Mencarelli, Massa Carrara, all of
(IT) --

Signed and Sealed this

First Day of January, 2002

Attest:

JAMES E. ROGAN
Attesting Officer
*Director of the United States Patent and Trademark Office*

US006206873C1

(12) EX PARTE REEXAMINATION CERTIFICATE (7774th)
United States Patent
Paolini et al.

(10) Number: US 6,206,873 C1
(45) Certificate Issued: Sep. 28, 2010

(54) DEVICE AND METHOD FOR ELIMINATING ADIPOSE LAYERS BY MEANS OF LASER ENERGY

(76) Inventors: Cesare Paolini, Via Toscanini 7, 50066 Montanino di Reggello, Firenze (IT); Maurizio Maida, Via G. Solenghi, Milano (IT); Fabrizio Mencarelli, Via Meucci I/C, Massa Carrara (IT)

Reexamination Request:
No. 90/010,490, Apr. 9, 2009

Reexamination Certificate for:
Patent No.: 6,206,873
Issued: Mar. 27, 2001
Appl. No.: 09/322,579
Filed: May 28, 1999

Certificate of Correction issued Jan. 1, 2002.

Related U.S. Application Data

(63) Continuation-in-part of application No. 08/798,516, filed on Feb. 10, 1997, now Pat. No. 5,954,710.

(51) Int. Cl.
    *A61B 18/18* (2006.01)

(52) U.S. Cl. .................. 606/7; 606/15; 606/16
(58) Field of Classification Search ............ None
    See application file for complete search history.

(56) References Cited

U.S. PATENT DOCUMENTS

| | | | |
|---|---|---|---|
| 3,538,919 A | 11/1970 | Meyer | 606/36 |
| 4,537,193 A | 8/1985 | Tanner | |
| 4,686,979 A | 8/1987 | Gruen et al. | |
| 4,773,413 A | 9/1988 | Hussein et al. | |
| 4,985,027 A | 1/1991 | Dressel | |
| 5,084,043 A | 1/1992 | Hertzmann | |
| 5,102,410 A | 4/1992 | Dressel | |
| 5,123,845 A | 6/1992 | Vassiliadis et al. | |
| 5,129,896 A | 7/1992 | Hasson | |
| 5,334,190 A | 8/1994 | Seiler | |
| 5,370,642 A | 12/1994 | Keller | |
| 5,470,330 A | 11/1995 | Goldenberg et al. | |
| 5,531,739 A | 7/1996 | Trelles | 606/2.5 |
| 5,649,924 A | 7/1997 | Everett et al. | |
| 5,738,680 A | 4/1998 | Luther | |
| 5,807,385 A | 9/1998 | Keller | |
| 6,106,516 A | 8/2000 | Massengill | |
| 6,176,854 B1 | 1/2001 | Cone | |

OTHER PUBLICATIONS

Brochure for Sunrise Technologies, Inc. on the SunLase Dental Laser System, © 1993, pp. 1–2.
Doheny, Kathleen, "Laser Liposuction May Speed Process, Cause Less Pain," *Los Angeles Times*, Jul. 28, 1992, 1 page.
Brochure for Sunlase Dental Laser, Sunrise Technologies, 1993 (pp. 1–10).
Dressel, Thomas, M.D., "Laser Lipoplasty: A Preliminary Report," Lipoplasy Society Newsletter, Jul. 1990 (1 page).
Dressel, Thomas, M.D., "Laser Liposuction," Lasers in Surgery and Medicine Supplement, 1991 (1 page).
Apfelberg et al., Progress Report on Multicenter Study of Laser–Assisted Liposuction, Aesth. Plast. Surg. 18:259–64 (1994).
White et al., Use of the Pulsed Nd:Yag Laser for Intraoral Soft Tissue Surgery, Lasers in Sug. and Med. 11:455–461 (1991)
Osyris Medical pages at www.osyrismedicalusa.com (2009).
Elime Medical pages at www.smoothshapes.com (2009).
Apfelberg, Results of Multicenter Study of Laser–Assisted Liposuction, Clinics in Plast. Surg. vol. 23, No. 4, 713–719 (1996).

*Primary Examiner*—Beverly M. Flanagan

(57) ABSTRACT

A device and method for the removal of subcutaneous adipose layers with a laser source, optical fiber for conveying the laser ben emitted by the first source and a hollow needle f or guiding the fiber. The fiber ends in the vicinity of the end of the needle. The laser beam is generated with an intensity and a wavelength for liquefying, and maintaining liquid, the adipose cells. The laser beam from the optical fiber irradiates adipose cells in the adipose layer to transform the adipose cells into, and maintain the adipose cells as, a liquid substance.

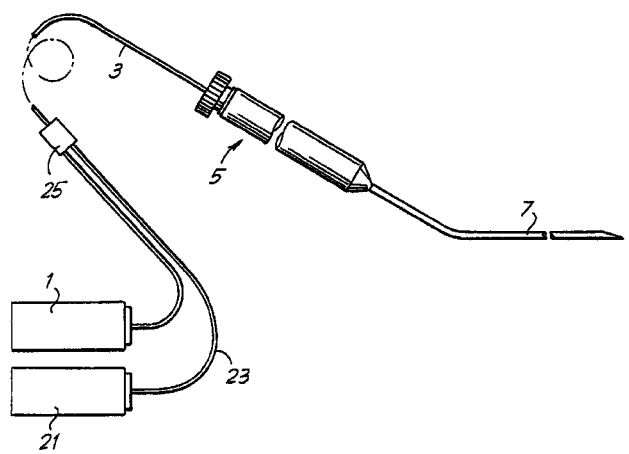

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2 and 8-16 is confirmed.

New claims 20-31 are added and determined to be patentable.

Claims 3-7 and 17-19 were not reexamined.

*20. A method for the removal of subcutaneous adipose layers, the method comprising the steps of:*
  *providing a hollow needle with a tip;*
  *providing a laser source with emitting characteristics for generating a laser beam having an intensity and a wavelength for causing lipolysis of adipose cells;*
  *generating a laser beam with said laser source;*
  *arranging an optical fiber inside said needle with one end of said optical fiber adjacent to said tip of said needle and with another end of said fiber connected to an output of said laser source, wherein the needle has an opening at the tip and the fiber extends through the opening;*
  *piercing the skin of a patient and bringing said needle tip into a subcutaneous adipose layer of the patient;*
  *irradiating said adipose layer with said laser beam to cause lipolysis of said adipose layer and rupturing membranes of cells forming the adipose layer, thus transforming adeps forming said adipose layer into a liquid substance.*

*21. The method of claim 20, wherein the fiber ends in the vicinity of the end of the needle.*

*22. A method for treating adipose cells in a patient, the method comprising the steps of:*
  *providing a hollow needle with a tip and an optical fiber inside said needle with one end of said optical fiber adjacent to said tip of said needle, wherein the needle has an opening at the tip and the fiber extends through the opening;*
  *generating a laser beam through said optical fiber with an intensity and a wavelength for liquefying, and maintaining liquid, the adipose cells;*
  *moving said tip of said needle into a subcutaneous adipose layer of the patient;*
  *irradiating adipose cells in the adipose layer with said laser beam from said optical fiber to transform the adipose cells into, and maintain the adipose cells as, a liquid substance.*

*23. The method of claim 22, wherein the fiber ends in the vicinity of the end of the needle.*

*24. A method for the removal of subcutaneous adipose layers, the method comprising the steps of:*
  *providing a hollow needle with a tip;*
  *providing a laser source with emitting characteristics for generating a laser beam having an intensity and a wavelength for causing lipolysis of adipose cells;*
  *generating a laser beam with said laser source;*
  *arranging an optical fiber inside said needle with one end of said optical fiber adjacent to said tip of said needle and with another end of said fiber connected to an output of said laser source;*
  *piercing the skin of a patient and bringing said needle tip into a subcutaneous adipose layer of the patient;*
  *irradiating said adipose layer with said laser beam to cause lipolysis of said adipose layer and rupturing membranes of cells forming the adipose layer, thus transforming adeps forming said adipose layer into a liquid substance; and*
  *removing the needle and the fiber from the adipose layer such that the liquid substance remains therein.*

*25. A method for treating adipose cells in a patient, the method comprising the steps of:*
  *providing a hollow needle with a tip and an optical fiber inside said needle with one end of said optical fiber adjacent to said tip of said needle;*
  *generating a laser beam through said optical fiber with an intensity and a wavelength for liquifying, and maintaining liquid, the adipose cells;*
  *moving said tip of said needle into a subcutaneous adipose layer of the patient;*
  *irradiating adipose cells in the adipose layer with said laser beam from said optical fiber to transform the adipose cells into, and maintain the adipose cells as, a liquid substance; and*
  *removing the needle and the fiber from the adipose layer such that the liquid substance remains therein.*

*26. A method for the removal of subcutaneous adipose layers, the method comprising the steps of:*
  *providing a hollow needle with a tip;*
  *providing a laser source with emitting characteristics for generating a laser beam having an intensity and a wavelength for causing lipolysis of adipose cells;*
  *generating a laser beam with said laser source;*
  *arranging an optical fiber inside said needle with one end of said optical fiber adjacent to said tip of said needle and with another end of said fiber connected to an output of said laser source;*
  *piercing the skin of a patient and bringing said needle tip into a subcutaneous adipose layer of the patient;*
  *irradiating said adipose layer with said laser beam to cause lipolysis of said adipose layer and rupturing membranes of cells forming the adipose layer, thus transforming adeps forming said adipose layer into a liquid substance; and*
  *removing the liquid substance away from the adipose layer with another tool inserted through the skin of the patient.*

*27. A method for treating adipose cells in a patient, the method comprising the steps of:*
  *providing a hollow needle with a tip and an optical fiber inside said needle with one end of said optical fiber adjacent to said tip of said needle;*
  *generating a laser beam through said optical fiber with an intensity and a wavelength for liquefying, and maintaining liquid, the adipose cells;*
  *moving said tip of said needle into a subcutaneous adipose layer of the patient;* irradiating adipose cells in the adipose layer with said laser beam from said optical fiber to transform the adipose cells into, and maintain the adipose cells as, a liquid substance; and removing the liquid substance away from the adipose layer with another tool inserted through the skin of the patient.

28. A method for the removal of subcutaneous adipose layers, the method comprising the steps of:

providing a hollow needle with a tip;

providing a laser source with emitting characteristics for generating a laser beam having an intensity and a wavelength for causing lipolysis of adipose cells;

generating a laser beam with said laser source;

arranging an optical fiber inside said needle with one end of said optical fiber adjacent to said tip of said needle and with another end of said fiber connected to an output of said laser source;

piercing the skin of a patient and bringing said needle tip into a subcutaneous adipose layer of the patient such that the end of the fiber comes directly into contact with the adipose layer;

irradiating said adipose layer with said laser beam to cause lipolysis of said adipose layer and rupturing membranes of cells forming the adipose layer, thus transforming adeps forming said adipose layer into a liquid substance.

29. A method for treating adipose cells in a patient, the method comprising the steps of:

providing a hollow needle with a tip and an optical fiber inside said needle with one end of said optical fiber adjacent to said tip of said needle such that the end of the fiber comes directly into contact with the adipose layer;

generating a laser beam through said optical fiber with an intensity and a wavelength for liquefying, and maintaining liquid, the adipose cells;

moving said tip of said needle into a subcutaneous adipose layer of the patient;

irradiating adipose cells in the adipose layer with said laser beam from said optical fiber to transform the adipose cells into, and maintain the adipose cells as, a liquid substance.

30. The method of claim 1, wherein the irradiating includes using the laser to maintain the adipose cells at the adipose layer as a liquid.

31. The method of claim 13, further comprising irradiating the adipose layer with another laser beam for providing transcutaneous vision.

* * * * *